United States Patent
Chene et al.

(10) Patent No.: US 10,634,934 B2
(45) Date of Patent: Apr. 28, 2020

(54) METHOD FOR DETERMINING A GEOMETRICAL PARAMETER OF AN EYE OF A SUBJECT

(71) Applicant: ESSILOR INTERNATIONAL (Compagnie Generale d'Optique), Charenton-le-Pont (FR)

(72) Inventors: Sylvain Chene, Charenton-le-Pont (FR); Romain Fayolle, Charenton-le-Pont (FR)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 41 days.

(21) Appl. No.: 15/723,783

(22) Filed: Oct. 3, 2017

(65) Prior Publication Data

US 2018/0095295 A1 Apr. 5, 2018

(30) Foreign Application Priority Data

Oct. 4, 2016 (EP) .................... 16306302

(51) Int. Cl.
*G02C 7/02* (2006.01)
*A61B 3/107* (2006.01)
(Continued)

(52) U.S. Cl.
CPC ............ *G02C 7/027* (2013.01); *A61B 3/0025* (2013.01); *A61B 3/107* (2013.01); *A61B 3/113* (2013.01);
(Continued)

(58) Field of Classification Search
CPC ....... G02C 7/027; A61B 3/0025; A61B 3/107; A61B 3/113; A61B 3/14; A61B 3/112;
(Continued)

(56) References Cited

U.S. PATENT DOCUMENTS 4,973,149 A * 11/1990 Hutchinson ............ A61B 3/113
351/210
7,515,054 B2 4/2009 Torch
(Continued)

FOREIGN PATENT DOCUMENTS

CN 1960670 5/2007
CN 101419664 4/2009
(Continued)

OTHER PUBLICATIONS

EP Search Report, dated Mar. 30, 2017, from corresponding EP 16 30 6302 application.
(Continued)

*Primary Examiner* — Mia M Thomas
(74) *Attorney, Agent, or Firm* — Young & Thompson

(57) ABSTRACT

The invention provides a method for determining a geometrical parameter of an eye of a subject, such as for determining the position of a center of rotation of the subject's eye, such as for the purpose of personalizing the optical design of corrective ophthalmic lenses, wherein at least two images of the eye are captured with an image capture device while the subject looks in two different gaze directions, and on each image, the pupil and/or the iris of the eye are identified so that a geometrical parameter may be determined for determining a position of a center of rotation of the eye without requiring use of a reference accessory.

20 Claims, 3 Drawing Sheets

(51) Int. Cl.
*A61B 3/14* (2006.01)
*A61B 3/00* (2006.01)
*A61B 3/113* (2006.01)
*G06T 7/73* (2017.01)
*A61B 3/11* (2006.01)
*G16H 50/50* (2018.01)

(52) U.S. Cl.
CPC ............... *A61B 3/14* (2013.01); *A61B 3/112* (2013.01); *G06T 7/74* (2017.01); *G06T 2207/30041* (2013.01); *G16H 50/50* (2018.01)

(58) Field of Classification Search
CPC .. G06T 7/74; G06T 2207/30041; G16H 50/50
See application file for complete search history.

(56) References Cited

U.S. PATENT DOCUMENTS

| | | | |
|---|---|---|---|
| 7,862,172 | B2 | 1/2011 | Yoshinaga et al. |
| 8,885,882 | B1* | 11/2014 | Yin ............ G06F 3/00 382/103 |
| 9,033,496 | B2* | 5/2015 | Divo ............ G02C 13/005 351/204 |
| 9,160,929 | B2* | 10/2015 | Ro ............ H04N 5/23296 |
| 9,378,584 | B2* | 6/2016 | Gravois ............ G06T 19/006 |
| 9,775,512 | B1* | 10/2017 | Tyler ............ A61B 3/113 |
| 9,807,383 | B2* | 10/2017 | Crispin ............ G02B 27/017 |
| 9,898,082 | B1* | 2/2018 | Greenwald ............ G06F 3/013 |
| 10,074,031 | B2* | 9/2018 | Krenzer ............ G06K 9/4633 |
| 10,108,260 | B2* | 10/2018 | Park ............ G06T 7/80 |
| 2005/0175218 | A1* | 8/2005 | Vertegaal ............ A61B 3/113 382/103 |
| 2010/0013949 | A1* | 1/2010 | Miyamoto ............ A61B 3/113 348/222.1 |
| 2010/0056274 | A1* | 3/2010 | Uusitalo ............ G02B 27/017 463/31 |
| 2012/0133891 | A1* | 5/2012 | Jiang ............ H04N 5/3535 351/210 |
| 2012/0169596 | A1 | 7/2012 | Zhuang |
| 2013/0002846 | A1 | 1/2013 | De Bruijn et al. |
| 2013/0131985 | A1* | 5/2013 | Weiland ............ G01C 21/20 701/516 |
| 2015/0124214 | A1* | 5/2015 | Contet ............ G02C 7/027 351/204 |
| 2015/0154758 | A1 | 6/2015 | Nakazawa et al. |
| 2016/0026863 | A1* | 1/2016 | Hakoshima ............ H04N 13/239 382/103 |
| 2016/0342206 | A1* | 11/2016 | Shazly ............ A61B 5/1114 |
| 2016/0342856 | A1 | 11/2016 | Krenzer et al. |
| 2017/0003523 | A1* | 1/2017 | Petignaud ............ G02C 13/005 |
| 2017/0014026 | A1* | 1/2017 | Guyton ............ A61B 3/113 |
| 2017/0032214 | A1* | 2/2017 | Krenzer ............ G06K 9/00335 |
| 2017/0090220 | A1* | 3/2017 | Bonnin ............ A61B 3/113 |
| 2018/0125404 | A1* | 5/2018 | Bott ............ A63F 13/213 |

FOREIGN PATENT DOCUMENTS

| | | |
|---|---|---|
| CN | 102548465 | 7/2012 |
| EP | 2 826 414 | 1/2015 |
| EP | 2 976 990 A1 | 1/2016 |
| JP | 2004 062393 A | 2/2004 |
| WO | 2015/117904 A1 | 8/2015 |

OTHER PUBLICATIONS

Ankit Mathur, et al., Pupil shape as viewed along the horizontal visual field, Journal of Vision, May 2013, pp. 1-8, vol. 13, Issue 6.
Cathleen Fedtke, et al., The entrance pupil of the human eye: a three-dimensional model as a function of viewing angle, Optics Express, Oct. 2010, pp. 1-13, vol. 18, No. 21.
Chinese Office Action for Application No. 201710929403.8 dated Apr. 2, 2019.
Office Action issued in Chinese Patent Application No. 201710929403.8 dated Jan. 6, 2020 with English translation provided.

* cited by examiner

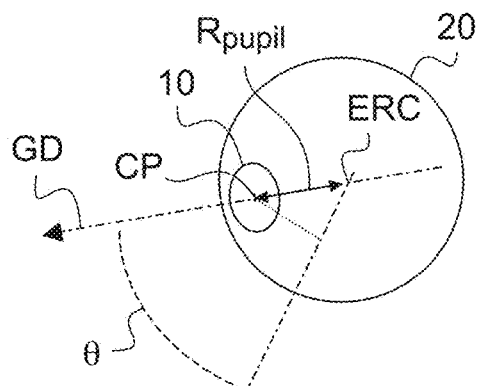
Fig.1
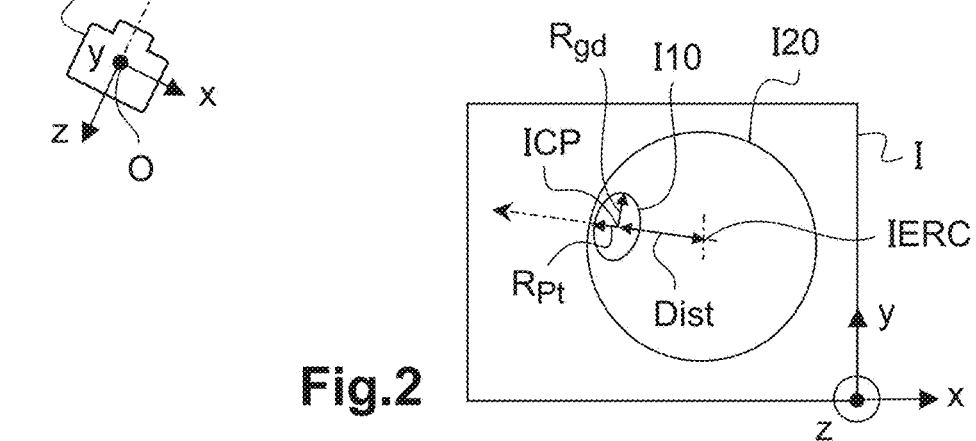
Fig.2
Fig.3
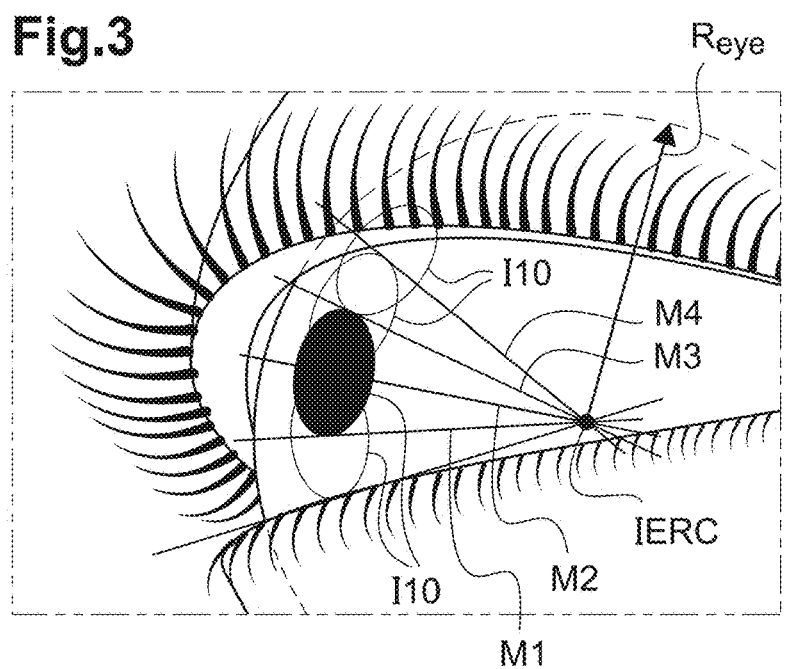

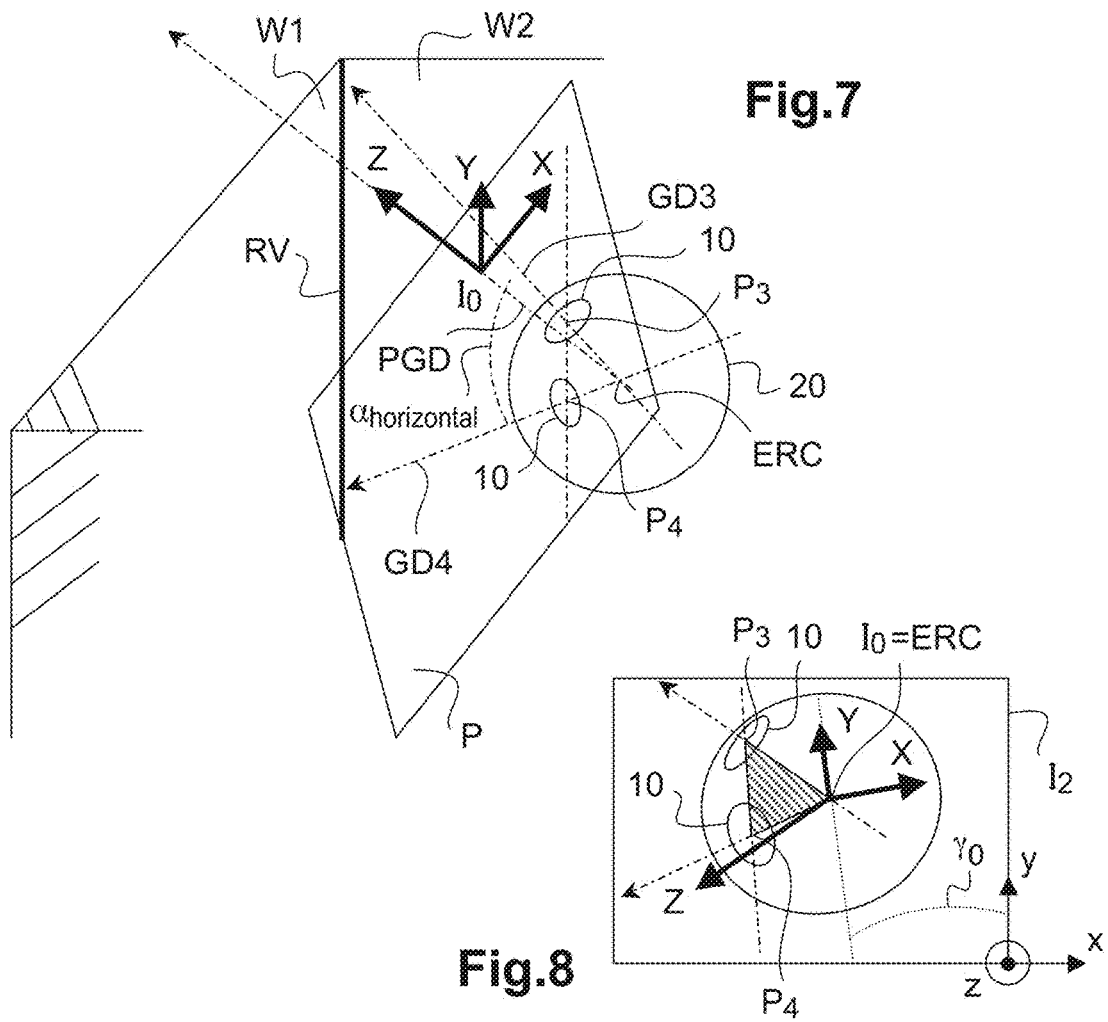
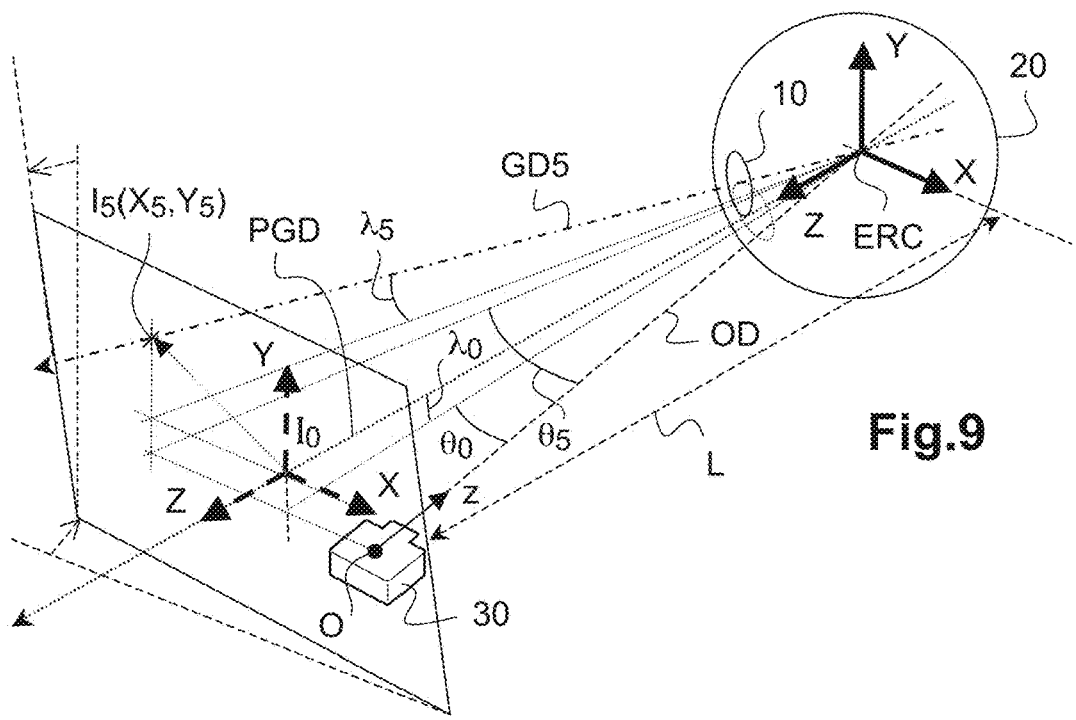

METHOD FOR DETERMINING A GEOMETRICAL PARAMETER OF AN EYE OF A SUBJECT

TECHNICAL FIELD OF THE INVENTION

The invention relates to a method for determining a geometrical parameter of an eye of a subject.

BACKGROUND INFORMATION AND PRIOR ART

The present invention relates in general to taking geometrico-morphological measurements of a subject.

More particularly, the invention relates to a method of determining a geometrical parameter of an eye of a subject.

A particular, but non-exclusive, application of the invention lies in taking geometrico-morphological measurements on a future subject of eyeglasses for the purpose of personalizing the optical design of the corrective ophthalmic lenses that are to be mounted in the frame selected by said future subject.

In order to customize the ophthalmic lens for a specific subject, geometrical, postural and behavioral parameters of the subject and/or of the subject with its eyeglasses need to be determined.

Among these parameters, the position of a center of rotation of at least one of the eye is determined.

Movement of the eye can generally be considered as being a combination of rotations about a particular point that is referred to as the center of rotation of the eye (ERC).

It is desirable to determine the position of this point, for example to perform calculations of a personalized optical design by ray tracing for the corrective lens that is to be fitted to the frame properly.

In present practice, the position of the ERC may be deduced approximately from the position of the cornea by assuming a mean value for the radius of the eye, typically a value of about 15 millimeters (mm). Unfortunately, the radius of the eye varies significantly from one individual to another, such that this approximation leads to significant errors that are highly penalizing for the pertinence of the personalized optical design calculation.

In order to determine the position of this center of rotation, it is also known to capture at least two facial images of the subject equipped with a reference accessory referred to as a position-identification element while the subject looks at the image capture device.

These images are treated in order to determine the center of rotation of the eye. The reference accessory gives information on the relative position of the head of the subject and the image capture device.

SUMMARY OF THE INVENTION

Therefore one object of the invention is to provide a method to determine quickly the position of the center of rotation of the eye, in a natural posture, without using a reference accessory.

This object is achieved according to the invention by providing a method for determining a geometrical parameter of an eye of a subject, comprising the following steps:

a) capturing at least two images of the eye while the subject looks in two different gaze directions thanks to an image capture device, b) identifying, on each image, the image of the pupil of the eye and determining a geometrical feature of the image of the pupil linked to the shape of this image of the pupil, c) determining said geometrical parameter of the eye as a function of said geometrical features of the image of the pupil determined for each image of said plurality of images.

Thanks to the invention, the geometrical parameter of the eye is determined quickly and in a simple manner, based on two images of the eye, without the use of a reference accessory. The method according to the invention indeed only requires one image capture device to be implemented.

In particular, the method according to the invention allows determining the position the center of rotation of the eye of the subject, relative to the image capture device.

It also allows determining the position of the center of rotation of the eye relative to an eyewear frame or relative to an instrument. This may be useful in order to take measurements for adjusting the optical equipment to the shape of the face of the subject.

Thank to the method according to the invention, these goals may be achieved even in the case of an image capture device placed very close to the eye of the subject, for example for an image capture device placed 2 cm away from the eye.

Other advantageous and non limiting features of the method according to the invention are as follows:

in step a), the two different gaze directions are spaced apart by at least 30 degrees of angle;

in step b), the outline of the image of the pupil and/or the iris is determined on each of said images and said geometrical feature of the image of the pupil and/or the iris is linked to the shape of this outline;

in step b), the outline of the image of the pupil and/or the iris being approximated by a model ellipse, the geometrical feature of the image of the pupil or the iris determined comprises the direction of at least one of the minor and major axis of the corresponding model ellipse, and/or a geometrical feature linked to the eccentricity of the model ellipse;

in step c), the geometrical parameter of the eye determined comprises a position of the center of rotation of the eye relative to said image capture device;

in step c), the images of the eye are superposed, the position of at least one intersection point between the minor axis of each of the model ellipse associated to the outline of the images of the pupils and/or the irises is determined and the position of the center of rotation of the eye is deduced from the position of said intersection point determined;

in step c), the position of the image of the center of rotation of the eye is identified to the position of a mean intersection point of all the minor axis of the model ellipses associated to the images of the pupil and/or the iris determined;

in step a), a plurality of images of the eye comprising more than two images, preferably more than five images, preferably more than ten images is captured while the subject looks at directions that are distinct for each image captured;

in step c), the geometrical parameter of the eye determined comprises a distance relative to a dimension of the eye and/or a distance between a center of rotation of the eye and an image capture device and/or a angle between an optical axis of an image capture device and a gaze axis and/or a direction of the gaze axis and/or a position of a point of intersection between a lens of eyeglasses placed on front of the eye and the gaze axis;

in step c), a predetermined model of the eye is taken into account;

said predetermined model of the eye comprises a circular model pupil or iris adapted to rotate about a model center of rotation at a given distance of this model center of rotation;

in step b), the outline of the image of the pupil and/or iris is determined on each of said images and said geometrical feature of the image of the pupil and/or iris is linked to the shape of this outline, and in step c), said geometrical parameter of the eye is determined by determining a theoretical geometrical feature of the image of the pupil or iris on the captured image as a function of the geometrical parameter of the eye looked for, on the basis of the predetermined model of the eye, minimizing the difference between the theoretical geometrical feature of the image of the pupil or iris and the geometrical feature of the image of the pupil or iris in the image captured determined in step b);

in step a), the eye of said subject stares at a lighting source while said at least two images of the eye are captured, and a position of the image of the corneal reflection of the lighting source is determined;

in step a), said image capture device is placed less than 2 centimeters away from the eye, preferably less than 1 centimeter away from the eye;

in step a), said image capture device is placed laterally on one side of the eye; and, in step a), said image capture device is placed on the head or on a frame placed on the head of the subject.

DETAILED DESCRIPTION OF EXAMPLE(S)

The following description made with reference to the accompanying drawings given by way of non-limiting example makes it clearly understood what the invention consists in and how it can be reduced to practice.

In the accompanying drawings:

FIG. 1 is a schematic representation of an eye and an image capture device in space;

FIG. 2 is a schematic representation of an image captured by the image capture device of FIG. 1;

FIG. 3 is a schematic view of a superposition of images for the determination of the center of rotation of the eye;

Figure 4:
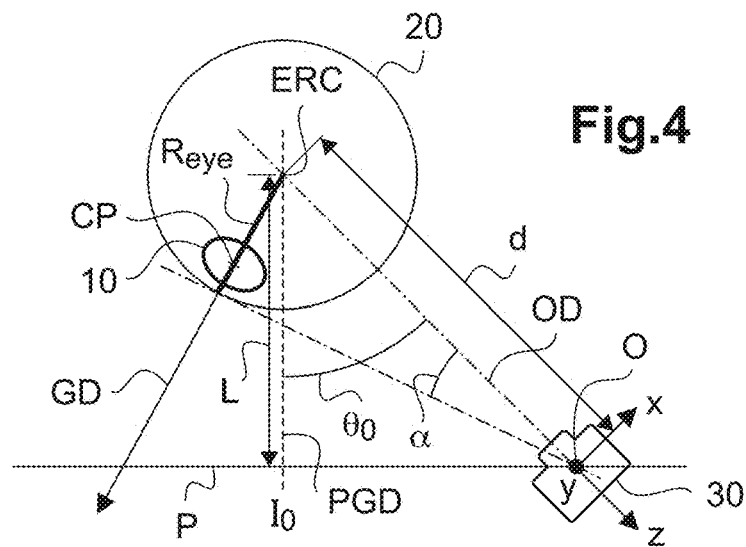
Figure 5:
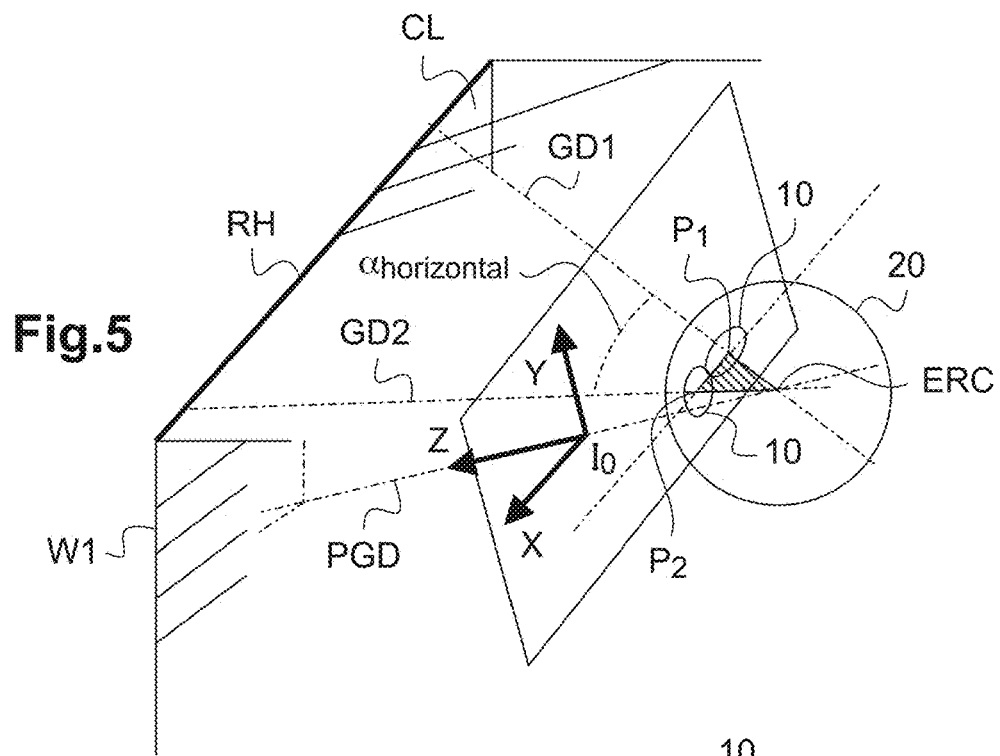
Figure 6:
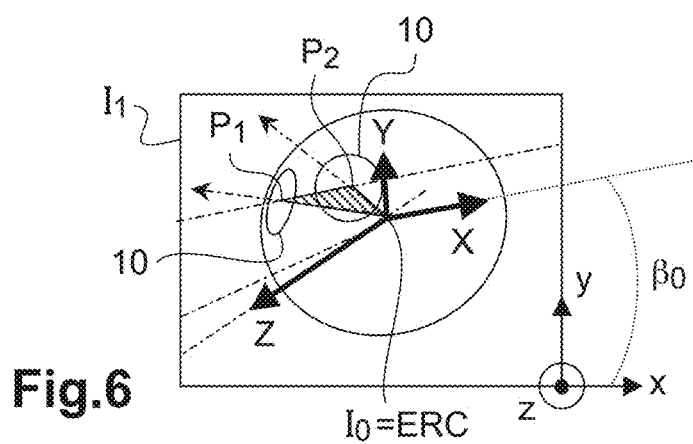

FIG. 4 is a schematic representation of an eye, a lens and the image capture device, FIG. 5 is a schematic representation of an eye in space in two positions corresponding to the eye looking at two points of a horizontal line, FIG. 6 is a schematic representation of the superposition of the two images captured in the two position of the eye on FIG. 5, FIG. 7 is a schematic representation of an eye in space in two positions corresponding to the eye looking at two points of a vertical line, FIG. 8 is a schematic representation of the superposition of the two images captured in the two position of the eye on FIG. 7, FIG. 9 is a schematic representation of the eye and the lens placed in front of this eye for determining the intersection I1 of the gaze direction of the eye and the lens.

In order to customize an ophthalmic lens for a specific subject, many geometrical and/or physiological and/or postural and/or behavioral parameters of the subject are determined. Some features of the frame and/or some parameters relative to the placement of the frame on the head of the subject may as well be taken into account.

The determination of the values of many of these parameters require the determination of a geometrical parameter of the eye of the subject, for example of the position of the center of rotation of the eye of the subject, in a referential.

This geometrical parameter of the eye of the subject may be determined according to the invention, through the following steps:

a) capturing at least two images of the eye while the subject looks in two different gaze directions thanks to an image capture device, b) identifying, on each image, the image of the pupil and/or of the iris of the eye and determining a geometrical feature of the image of the pupil and/or of the iris linked to the shape of this image of the pupil and/or the iris, c) determining said geometrical parameter of the eye as a function of said geometrical features of the image of the pupil and/or the iris determined for each image of said plurality of images.

Thanks to the invention, the geometrical parameter of the eye is determined quickly and in a simple manner, based on two images of the eye, without the use of a reference accessory. The method according to the invention indeed only requires one image capture device to be implemented.

In practice, in order to achieve an improved accuracy on the determination of the geometrical parameter of the eye, more than two images are captured and treated as described below, for example at least three images, at least five, at least 10 images or more than 10 images.

Step a)

More precisely, step a) comprises the following sub-steps:

a1) placing the eye of the subject in a first relative posture relative to the entry pupil of the image capture device;

a2) in said first relative posture, capturing a first plane image of the eye by means of the image capture device;

a3) placing the eye of the subject in a second relative posture relative to the entry pupil of the image capture device, the second relative posture being distinct from the first relative posture;

a4) in the second relative posture, capturing a second plane image of the eye by means of the image capture device.

The gaze direction is the direction in which the subject is looking. It may be defined as the axis going through the center of rotation of the eye and the center of the pupil of the eye. The gaze direction also goes through the sighting point fixed by the subject.

Advantageously, the two different gaze directions are spaced apart by at least 30 degrees of angle.

This ensures a satisfactory accuracy in determining the geometrical feature of the eye based on these two images.

In practice, this is achieved preferably by capturing a plurality of images of the eye while the subject moves his eyes, while the image capture device remains at a fixed position compared to the eye.

Said image capture device is placed on the head of the subject.

More precisely, according to the method of the invention, the image capture device is preferably attached to the head of the subject.

It is for example placed on a support attached directly to the head of the subject. This support may be an eyeglasses frame placed on the head of the subject.

Said image capture device is for example placed laterally on one side of the eye. It may therefore be attached to the branch and/or the corresponding circle of the frame.

In these conditions, said image capture device is placed less than 2 centimeters away from the eye, preferably less than 1 centimeter away from the eye.

Moreover, consequently, the relative position of the image capture device and the head of the subject is fixed during the capture of said plurality of images.

The image capture device is for example a camera, preferably a movie camera.

In order to ensure that the gaze direction of the eye of the subject is different during each image capture, provision can then be made for the eye to look respectively at first and second sighting points, while capturing the first and second images.

In practice, one may ask the subject to gaze at a moving sighting point while capturing the plurality of images of the eye.

The plurality of images captured is transmitted to a computer unit. The image capture device may be integrated with this computer unit or form an independent element.

By controlling the movement of the sighting point, one may control the movement of the eye of the subject and make sure that each image of the plurality of images captured corresponds to a different gaze direction.

The capture of a plurality of images of the eye may be performed during a specific calibration step, during which the subject is asked to gaze at the moving sighting point, or it may be performed continuously while tracking the eye of the subject with an eye-tracking device. In that last case, the eye-tracking device may be calibrated in real time in order to correct any movement of the eye-tracking device relative to the eye.

Preferably, in step a), a plurality of images of the eye comprising more than two images, preferably more than five images, preferably more than ten images is captured while the subject looks at directions that are distinct for each image captured.

Preferably, in step a), a plurality of images of a side view of the eye is captured.

Step b)

In each of said first and second images, the image of a pupil and/or an iris of the eye is identified.

This identification may be performed by any known conventional image treatment method, such as edge detection algorithms.

In practice, the computer unit is programmed to identify the image of the pupil and/or the iris of the eye of the subject in each of the plurality of images captured.

Once the image of the pupil and/or of the iris has been identified, the computer unit is programmed to determine a geometrical feature of the image of the pupil and/or the iris linked to the shape of this image of the pupil and/or the iris.

In general, the optical axis of the image capture device and the gaze direction are not superposed, meaning that the pupil of the image capture device is offset compared to the gaze direction.

A simple model of the eye comprises a circular pupil or iris, moving in rotation about the center of rotation of the eye, at a constant distance of this center of rotation, that is to say on a sphere of radius equal to $R_{pupil}$.

For this reason, the image of the pupil and/or the iris of the subject on the image captured usually presents an elliptic shape.

In the example shown on the figures and described below, only a first embodiment of the method based on the shape of the pupil of the subject will be described, the method based on the shape of the iris being identical.

The eye 20 of the subject is represented in space on FIG. 1. It is represented here by the location where the pupil 10 of the subject moves when the subject moves his eye.

The actual radius of the eye $R_{eye}$ is in fact slightly bigger than the radius $R_{pupil}$ of the location where the pupil moves.

The gaze direction GD of the subject goes through the center CP of the pupil 10 of the subject and the center of rotation ERC of the eye 20.

A referential (O, x, y, z) of the image capture device 30 is placed relative to the eye 20. The axis (O, z) links the pupil of the image capture device and the center of rotation of the eye. This axis will also be called below the observation axis OD.

A tilt angle θ lies between the observation axis and the gaze direction.

The distance between the center CP of the pupil 10 and the center of rotation ERC of the eye 20 is the radius $R_{pupil}$ of the location where the pupil moves.

FIG. 2 shows the corresponding image I captured by the image capture device with the gaze direction GD forming the angle θ with the observation axis OD. The image I10 of the pupil of the subject is shown in the image I20 of the eye of the subject. The image is then captured in the plane (O, x, y) of said referential linked to the image capture device 30.

As shown on FIG. 2, the image I10 of the pupil of the eye of the subject on the image I captured has the shape of an ellipse of center ICP. The outline of the image of the pupil I10 is therefore close to an ellipse.

Said geometrical feature of the image of the pupil is linked to the shape of the outline of the image I10 of the pupil.

This outline is determined by the computer unit, for example by an edge detection method. The computer unit is then programmed for determining said geometrical feature of the image of the pupil I10.

More precisely, the outline of the image of the pupil being approximated by a model ellipse, the geometrical feature of the image of the pupil determined comprises the direction of at least one of the minor and major axis of the corresponding model ellipse, and/or a geometrical feature linked to the eccentricity of the model ellipse.

In the example here described, the computer unit is programmed to determine the minor and/or major axis of the ellipse corresponding to the outline of the pupil.

More precisely, the computer unit is programmed to determine the model ellipse closest to the outline of the pupil, and determine its minor and major axis.

The major axis of the ellipse is the longest diameter $R_{gd}$ of this ellipse, whereas the minor axis is the shortest diameter $R_{pt}$ of the ellipse.

The model ellipse is determined by the following features: coordinates (xc, yc) of its center, its eccentricity e and/or the distance from the center of the ellipse to the perimeter along the minor and major axis of the ellipse and the angle of tilt θ defined before.

The determination of the model ellipse is achieved by determining the five features of this model ellipse for which the corresponding ellipse goes through the higher number of points of the actual outline of the pupil determined. Advantageously, a step of verification of the quality of the outline of the pupil determine may be implemented. In this step, a quality factor may be determined based on:

the mean contrast of the image on each side of the outline determined, the size of the image I10 of the pupil, a comparison between the outline determined and the previous outlines determined before.

The quality factor will be higher for a higher difference of contrast between the two sides of the outline. The size of the image of the pupil may be compared to a theoretical size determined based on parameters of the image capture device: distance between the image capture device and the eye, focal distance of the image capture device. The quality factor is then higher when the size of the image of the pupil determined is closer to the theoretical size calculated.

The features of the outline determined by image treatment may also be compared to the outline determined for a previous image captured just before the current image treated, in order to determine if the features of the outline determined on the current image is consistent with the outline determined for the previous image. Based on the outline determined on the previous image and the movement of the eye (speed, trajectory), the variation of the outline between the two corresponding image capture may indeed be determined and an expected theoretical outline may be deduced. The quality factor will be higher with a higher consistence between the outline determined and the expected outline.

Said geometrical feature of the image of the pupil is linked to the shape of the outline of the image I10 of the pupil.

More precisely, the outline of the image I10 of the pupil being approximated by the model ellipse as described before, the geometrical feature of the image of the pupil determined comprises the direction of at least one of the minor and major axis of the corresponding model ellipse, and/or a geometrical feature linked to the eccentricity of the model ellipse.

The computer unit is therefore programmed to determine at least one of the minor and major axis of the corresponding model ellipse, and/or said geometrical feature linked to the eccentricity of the model ellipse.

Step c)

In the example described here, the geometrical parameter of the eye determined comprises a position of the center of rotation of the eye relative to said image capture device.

Alternatively, the geometrical parameter of the eye determined may comprise a distance relative to a dimension of the eye and/or a distance between a center of rotation of the eye and an image capture device and/or a angle between an optical axis of an image capture device and a gaze axis and/or a direction of the gaze axis and/or a position of a point of intersection between a lens of eyeglasses placed on front of the eye and the gaze axis.

Here, the computer unit is then programmed to determine the position of the center of rotation of the eye, for example according to the procedure described in the following. In this procedure, it is considered that:

there is only one center of rotation of the eye for all the possible rotation of the eye, distortions of the pupil through the cornea are known in the central and temporal fields, distortions of each image are known to be negligible or corrected, the position of the image capture device is fixed relative to the eye of the subject during the capture of the plurality of images, the actual shape of the pupil of the eye is circular.

In the example described here, in step c), the images of the eye are superposed and the position of at least one intersection point between the minor axis of two of the model ellipses associated to the outlines of the images of the pupils is determined.

The position of the center of rotation of the eye is deduced from the position of said intersection point determined.

This is represented for example on FIG. 3.

More precisely, the position of the image of the center of rotation IERC of the eye may be identified with the intersection point of the minor axis M1, M2, M3, M4 of the model ellipses associated with at least two images I10 of the pupil.

In particular, the position of the image of the center of rotation IERC of the eye is for example identified to the position of a mean intersection point of all the minor axis M1, M2, M3, M4 of the model ellipses associated to the images of the pupil determined.

Alternatively, the position of the image of the center of rotation may be determined as a barycenter of the intersection points of the minor axis M1, M2, M3, M4. This identification may be performed graphically (see FIG. 3), or by calculation.

With a calibration of the field of the image capture device, or with a known position of the image capture device relative to the frame on which it is fixed, the direction of the line going through the pupil of the image capture device and the center of rotation of the eye may be determined relative to the frame. The coordinates of the center of rotation in two dimensions in the image capture device referential are deduced.

The coordinates of the center of rotation in three dimensions may be deduced based on known optical features of the image capture device. Alternatively, the coordinates of the center of rotation of the eye in the referential of the image capture device may be transposed in a real space referential.

The change of referential is described below.

The determination of the position of the center of rotation of the eye is used in many situations.

It may be used for determining the gaze direction and/or its intersection with the lens of eyeglasses worn by the subject. The precision obtained is less than 2° of angle, for example 1° of angle in the central field.

The central field is for example defined as an angular zone centered on a primary gaze axis spreading over 30°, which corresponds to a central zone of the lens centered on the intersection of the primary gaze axis and the lens having a 15 millimeters diameter.

It may be used for designing a customized lens.

It may be used for calibrating an eye-tracking device integrated in the eyeglasses frame worn by the subject.

In that last case, the position of the center of rotation may be checked to determine a movement of the eyeglasses frame relative to the head of the subject.

Other geometrical parameters of the eye of the subject may be determined, for example, the radius of the eye.

As mentioned previously, the eye is approximately the location where the pupil of the subject moves when the subject moves his eye. The radius of the eye may be approximated to the radius of the location of the pupil when the subject moves his eye.

It is therefore possible to determine the radius of the eye by determining the distance between the center of rotation of the eye and the center of the model ellipse on one of the images captured. Preferably a mean distance between the center of rotation and the center of the model ellipse determined on each image captured is calculated.

For example, the actual pupil being circular with a radius equal to $R_{gd}$, the image of the pupil on the image captured has a radius along the major axis equal to $R_{gd}$ and a radius along the minor axis equal to $R_{pt}=R_{gd}*\cos(\theta)$ with $\theta$ the tilt angle between the gaze direction GD and the observation axis (FIGS. 1 and 2).

$R_{pupil}$ is the radius of the location of the pupil when the subject moves his eye and Dist the distance between the image of the center of the pupil and the image of the center of rotation of the eye, in pixels (FIG. 2).

The distance Dist is measured on the image (FIG. 2).

Then $R_{pupil}=Dist/\sin \theta=Dist/\sin (a \cos(R_{pt}/R_{gd}))$.

$R_{pupil}$ is then calculated in pixels.

Having determined $R_{pupil}$ and the coordinates of the image of the center of rotation IERC ($x_{cro}$, $y_{cro}$), the tilt angle $\theta$ of the gaze direction GD relative to the observation axis OD may be determined as $\theta = A \sin(Dist/R_{pupil})$.

The radius of the eye $R_{eye}$ may be estimated based on the radius $R_{pupil}$ of the location of the pupil.

In a variant, in order to determine the radius of the eye $R_{eye}$, in a first step the position of the center of rotation is determined as described before.

Then, with reference to FIG. 4, the operator marks the intersection $I_0$ of a primary gaze direction PGD and the lens P of the eyeglasses worn by the subject. The primary gaze direction is the gaze direction when the subject looks straight ahead.

Then the distance $OI_0$ between the mark $I_0$ and the image capture device placed at the origin O of the referential (O, x, y, z) linked to the image capture device, is determined (FIG. 4).

The image capture device 30 is here supposed to be placed approximately in the mean plane of the lens.

In a variant the mean plane of the lens may be replaced by a plane of know position relative to the image capture device.

The angle $\theta_0$ between the primary gaze direction PGD and the observation axis OD is determined as $\cos \theta_0=R_{pt}/R_{gd}$.

The distance d between the center of rotation ERC of the eye and the image capture device 30 is then calculated as $d=OI_0/\sin \theta_0$.

An angle $\alpha$ between the observation axis OD and the tangent to the eye 20 at the intersection between the gaze direction GD and the eye is measured in degrees on the captured image, thanks to a calibration of the image (FIG. 4).

Then the radius of the eye may be deduced as $R_{eye}=d*\sin \alpha$.

As a variant, this radius of the eye may for example be measured in pixels on the images captured.

The distance L between the center of rotation ERC and the lens P may also be determined as the distance between the center of rotation ERC and the point $I_0$ on FIG. 4, using the following formula: $OI_0/L=\tan \theta_0$.

The distance ELD between the eye and the lens (Eye Lens Distance) may be deduced by subtracting the radius of the eye $R_{eye}$ to the value of the distance between the center of rotation of the lens L as ELD=L−Reye.

The parameter for changing referential may be determined as follows.

Geometrical parameters of the eye such as position of the center of rotation, shapes of the image of the pupil when the eye moves, location of the pupils when the eye moves, observation axis, are determined, for example thanks to the method according to the invention.

For a reference direction of the gaze direction, for example the primary gaze direction, the mark of the point $I_0$ is noted on the lens.

As represented schematically on FIG. 5, at least two images of the eye are captured while the eye looks at a reference horizontal line RH of space. The images then corresponds to the two different gaze direction GD1, GD2 of FIG. 5, for the position P1 and P2 of the center of the pupil 10

This reference horizontal line may for example be the intersection between a wall W1 and the ceiling CL in a room. Preferably, the angle $\alpha_{horizontal}$ between the two gaze direction GD1 and GD2 is maximum, for example superior to 30°.

The axis going through the centers P1, P2 of the pupil 10 in these two images capture is taken as the ($I_0$, X) axis of the referential ($I_0$, X, Y, Z) of space linked to the gaze direction in real space.

FIG. 6 show the superposition I1 of the two images captured in the situation described in reference to FIG. 5.

As shown on this FIG. 6, an angle $\beta_0$ exists between the ($I_0$, X) axis of the referential linked to the gaze direction in real space and the (O, x) axis linked to the image capture device.

In order to change referential from the referential linked to the gaze direction in real space ($I_0$, X) to the referential linked to the image capture device (O, x), the following matrix is determined:

$$Rz(\beta_0) = \begin{pmatrix} \cos\beta_0 & -\sin\beta_0 \\ \sin\beta_0 & \cos\beta_0 \end{pmatrix}.$$

In a similar manner, the change of referential may be determined for the vertical axis.

As represented schematically on FIG. 7, at least two images of the eye are captured while the eye looks at a reference vertical line RV of space. The images then corresponds to the two different gaze direction GD3, GD4 of FIG. 7, for the position P3 and P4 of the center of the pupil 10.

This reference vertical line may for example be the intersection between the wall W1 and another wall W2 in a room. Preferably, the angle $\alpha_{vertical}$ between the two gaze directions GD3 and GD4 is maximal, for example superior to 30°.

The axis going through the centers P3, P4 of the pupil 10 in these two images captured is taken as the ($I_0$, Y) axis of the referential ($I_0$, X, Y, Z) of space linked to the gaze direction in real space.

FIG. 8 show the superposition I2 of the two images captured in the situation described in reference to FIG. 7.

As shown on this figure, an angle $\gamma_0$ exists between the ($I_0$, Y) axis of the referential linked to the gaze direction in real space and the (O, y) axis linked to the image capture device.

In order to change referential from the referential linked to the gaze direction in real space ($I_0$, Y) to the referential linked to the image capture device (O, y), the following matrix is determined:

$$Rz(\gamma_0) = \begin{pmatrix} \cos\gamma_0 & -\sin\gamma_0 \\ \sin\gamma_0 & \cos\gamma_0 \end{pmatrix}.$$

The referential (I0, X, Y) is projected on the lens P.

The change of referential may be performed between the image capture device and the boxing referential. The X axis is then marked by a checkerboard test pattern imaged by the image capture device. The checkerboard test pattern is placed perpendicularly to the horizontal plane formed by the branches of the eyeglasses frame.

A useful application is to determine the gaze direction, its intersection with the plane P of the lens and usage area of the lens.

With reference to FIG. 9, an approximated calculation of the coordinates (X5, Y5) of the intersection point $I_5$ between a gaze direction GD5 and the lens P may be achieved as $X_5 = L*\tan(\theta_5 - \theta_0)$, $Y_5 = L*\tan(\lambda_5 - \lambda_0)$. The angle $\theta_0$ is measured between the observation axis OD and its projection in the $(I_0, Y, Z)$ plane of the referential. The angle $\theta_5$ is measured between the observation axis OD and the projection of the gaze direction GD5 in the $(I_0, X, Z)$ plane. The angle $\lambda_0$ is measured between the primary gaze axis PGD and the projection of the observation axis OD the $(I_0, Y, Z)$ plane of the referential. The angle $\lambda_5$ is measured between the gaze direction GD5 and its projection in the $(I_0, X, Z)$ plane of the referential. In another embodiment of the method according to the invention, a more complete model of the eye is taken into account.

This advantageously allows taking into account:

the fact that the pupil has a different shape when the image capture device is placed on the temporal side of the eye or on the nasal side of the eye, the fact that the eccentricity of the model ellipse corresponding to the outline of the pupil depends in a complex manner on the angle between the gaze direction and the observation axis defined before, the shape of the pupil may depend on the gaze direction, the convergence of the eye, the lighting conditions . . .

the pupil may exhibit a shape different from the circular shape.

Such a model of the eye may be found in the following publications: "*The entrance pupil of the human eye: a three-dimensional model as a function of viewing angle*" by authors: Cathleen Fedtke, Fabrice Manns, and Arthur Ho, published in OPTICS EXPRESS on Oct. 7, 2010 and "*Pupil shape as viewed along the horizontal visual field*" Ankit Mathur, Julia Gehrmann, David A. Atchison, published in Journal of Vision (2013) 13(6):3, 1-8.

In this embodiment taking into account a complete model of the eye, step a) is performed as described before. In step b), the outline of the image of the pupil is determined on each of said images and said geometrical feature of the image of the pupil is linked to the shape of this outline.

In the following, only the pupil will be taken into account.

In step c), said geometrical parameter of the eye is determined by determining a theoretical geometrical feature of the image of the pupil on the captured image as a function of the geometrical parameter of the eye looked for, on the basis of the predetermined model of the eye, minimizing the difference between the theoretical geometrical feature of the image of the pupil and the geometrical feature of the image of the pupil in the image captured determined in step b).

In the complete model of the eye, a general model of the pupil is implemented: this general model may be a constant circular pupil as taken into account in the previous example, or a more complex model, allowing the pupil to have a non circular shape, and/or a shape that changes over time, as a function of the light conditions or of the gaze direction for example. The general model of pupil is in rotation about the center of rotation ERC, at a distance of the center of rotation of the eye that may be approximated to the radius of the eye Reye.

In step b), in each captured image, the outline of the image of pupil is determined. By superposing all the images, the location of the image of the pupil during the rotation of the eye may also be determined.

The position of the image of the center of rotation of the eye and the radius of the image of the eye are determined based on the superposition of the captured images.

This distance is determined based on a superposition of a plurality of images. It is determined in pixels and converted into millimeters. The parameters of the general model of the pupil are determined based on each image captured.

The image of the gaze axis, going through the center of the image of the pupil and the image of the center of rotation of the eye is determined for each image.

The actual gaze axis may be deduced with a change of referential.

A theoretical shape of the image of the pupil corresponding to the actual gaze axis is determined. The outline of the image of the pupil determined is compared to this theoretical shape of the image of the pupil and the difference between this outline and the theoretical shape is deduced.

The position of the image of the center of rotation, the radius of the eye $R_{eye}$ determined and the parameters of the general model of the pupil are optimized by minimizing the differences between the outline of the pupil and the theoretical shape of the pupil for all the images captured and treated.

The method according to the invention is empirical and requires no information on the position of the image capture device and/or eyeglass frame relative to the head of the subject. It requires neither additional lighting devices nor information about their position relative to the head of the subject.

The position of the center of rotation is determined precisely.

Once the position of the center of rotation and the radius of the eye in the images are determined, other geometrical parameters of the eye may be determined by treating the images captured.

The trajectory of the corneal reflects of the sighting points relative to the pupil may be analyzed in order to determined a cartography of the corneal topography.

The method may be used in eye-trackers integrated to smart eyewear or instruments for opticians used to determine the mounting parameters of the subject or morphological-geometric parameters for designing customized lenses.

It may also be used in corneal analyzer for measuring eye parameters such as corneal topography, and divergence of the eyes.

The invention claimed is:

1. A method for determining a geometrical parameter of an eye (20) of a subject, comprising the following steps:
   a) capturing, with an image capture device (30), at least two images of the eye (20) while the subject looks in two different gaze directions (GD);
   b) identifying, on each of the at least two images, an image (I10) of at least one of a pupil (10) and an iris of the eye (20), and determining a geometrical feature of the image (I10) of the at least one of the pupil and the iris linked to a shape of said image (I10) of the at least one of the pupil and the iris, wherein an outline of the image (I10) of the at least one of the pupil and the iris is determined on each of said at least two images, and said geometrical feature of the image (I10) of the at least one of the pupil and the iris is linked to a shape of the outline; and c) determining said geometrical parameter of the eye (20) as a function of said geometrical feature of the image (I10) of the at least one of the pupil and the iris determined for each image of said at least two images.

2. The method according to claim 1, wherein, in step a), the two different gaze directions differ by an angle of at least 30 degrees.

3. The method according to claim 1, wherein, in step b), the outline of the image (I10) of the at least one of the pupil and the iris is approximated by a model ellipse, the geometrical feature of the image of the at least one of the pupil and the iris determined comprises a direction of at least one of minor (M1, M2, M3, M4) and major axes of at least one of the model ellipse and a geometrical feature linked to an eccentricity of the model ellipse.

4. The method according to claim 1, wherein, in step c), the geometrical parameter of the eye determined comprises a position of the center of rotation (ERC) of the eye (20) relative to said image capture device (30).

5. The method according to claim 4, wherein, in step c), the at least two images of the eye are superposed, a position of at least one intersection point between a minor axis (M1, M2, M3, M4) of each of the model ellipse associated to at least one of the outline of the images is determined, and the position of the center of rotation (ERC) of the eye (20) is deduced from the position of said determined intersection point.

6. The method according to claim 5, wherein, in step c), a position of the image of the center of rotation (IERC) of the eye is identified to a position of a mean intersection point of all determined minor axes (M1, M2, M3, M4) of the model ellipses associated to the images.

7. The method according to claim 1, wherein, in step a), a plurality of images of the eye comprising more than two images is captured while the subject looks at directions that are distinct for each image captured.

8. The method according to claim 7, wherein, in step a), a plurality of images of the eye comprising more than five images is captured.

9. The method according to claim 7, wherein, in step a), a plurality of images of the eye comprising more than ten images is captured.

10. The method according to claim 1, wherein, in step c), the determined geometrical parameter of the eye comprises a distance relative to at least one of a dimension of the eye ($R_{eye}$), a distance between a center of rotation of the eye and an image capture device (L), an angle between an observation axis (OD) linking the center of rotation of the eye and the image capture device and a gaze axis (GD), a direction of the gaze axis (GD), and a position of a point of intersection ($I_0$, $I_1$) between a lens (P) of eyeglasses placed on front of the eye and the gaze axis (GD).

11. The method according to claim 1, wherein, in step c), a predetermined model of the eye is taken into account.

12. The method according to claim 11, wherein said predetermined model of the eye comprises a circular model of one of a pupil and an iris, adapted to rotate about a model center of rotation at a given distance.

13. The method according to claim 11,
wherein, in step b), the outline of the image of the at least one of the pupil the iris is determined on each of said images and said geometrical feature of the image of the at least one of the pupil the iris is linked to the shape of the outline, and
wherein in step c), said geometrical parameter of the eye is determined by determining a theoretical geometrical feature of the image as a function of the geometrical parameter of the eye, on the basis of the predetermined model of the eye, and minimizing a difference between the theoretical geometrical feature of the image and the geometrical feature of the image determined in step b).

14. The method according to claim 1, wherein, in step a), the eye of said subject stares at a lighting source while said at least two images of the eye (20) are captured, and a position of the image of a corneal reflection of the lighting source is determined.

15. The method according to claim 1, wherein, in step a), said image capture device is placed less than 2 centimeters away from the eye.

16. The method according to claim 15, wherein, in step a), said image capture device is placed on the head or on a frame placed on the head of the subject.

17. The method according to claim 15, wherein, in step a), said image capture device is placed less than 1 centimeter away from the eye.

18. The method according to claim 1, wherein, in step a), said image capture device is placed laterally on one side of the eye.

19. A method for determining a geometrical parameter of an eye (20) of a subject, comprising the following steps:

a) capturing, with an image capture device (30), at least two images of the eye (20) while the subject looks in two different gaze directions (GD), the two different gaze directions differing by an angle of at least 30 degrees;

b) identifying, on each of the at least two images, an image (I10) of at least one of a pupil (10) and an iris of the eye (20), and determining a geometrical feature of the image (I10) of the at least one of the pupil and the iris linked to a shape of said image (I10) of the at least one of the pupil and the iris; and c) determining said geometrical parameter of the eye (20) as a function of said geometrical feature of the image (I10) of the at least one of the pupil and the iris determined for each image of said at least two images.

20. A method for determining a geometrical parameter of an eye (20) of a subject, comprising the following steps:

a) capturing, with an image capture device (30), at least two images of the eye (20) while the subject looks in two different gaze directions (GD);

b) identifying, on each of the at least two images, an image (I10) of at least one of a pupil (10) and an iris of the eye (20), and determining a geometrical feature of the image (I10) of the at least one of the pupil and the iris linked to a shape of said image (I10) of the at least one of the pupil and the iris; and c) determining said geometrical parameter of the eye (20) as a function of said geometrical feature of the image (I10) of the at least one of the pupil and the iris determined for each image of said at least two images, wherein, in step c), the geometrical parameter of the eye determined comprises a position of the center of rotation (ERC) of the eye (20) relative to said image capture device (30).

* * * * *